US010231970B2

(12) United States Patent
Lightner

(10) Patent No.: US 10,231,970 B2
(45) Date of Patent: Mar. 19, 2019

(54) METHODS OF PRODUCING HETEROPOLYCYCLES VIA BIS-EPOXIDATION

(71) Applicant: Derek Alton Lightner, Reno, NV (US)

(72) Inventor: Derek Alton Lightner, Reno, NV (US)

(73) Assignee: NV Heterocycles, Reno, NV (US)

(*) Notice: Subject to any disclaimer, the term of this patent is extended or adjusted under 35 U.S.C. 154(b) by 0 days.

(21) Appl. No.: 15/515,604

(22) PCT Filed: Sep. 30, 2015

(86) PCT No.: PCT/US2015/053066
§ 371 (c)(1),
(2) Date: Mar. 30, 2017

(87) PCT Pub. No.: WO2016/054123
PCT Pub. Date: Apr. 7, 2016

(65) Prior Publication Data
US 2017/0305907 A1 Oct. 26, 2017

Related U.S. Application Data

(60) Provisional application No. 62/057,939, filed on Sep. 30, 2014.

(51) Int. Cl.
A61K 31/4995 (2006.01)
A61K 31/407 (2006.01)
A61K 31/5386 (2006.01)
C07D 471/08 (2006.01)
C07D 487/08 (2006.01)
C07D 498/08 (2006.01)

(52) U.S. Cl.
CPC ........ A61K 31/4995 (2013.01); A61K 31/407 (2013.01); A61K 31/5386 (2013.01); C07D 471/08 (2013.01); C07D 487/08 (2013.01); C07D 498/08 (2013.01)

(58) Field of Classification Search
CPC .................................. A61K 31/4995
USPC .......................................... 546/122
See application file for complete search history.

(56) References Cited

U.S. PATENT DOCUMENTS

| 3,167,561 | A | 1/1965 | Sarett et al. |
| 3,905,979 | A | 9/1975 | Henry et al. |
| 3,947,445 | A | 3/1976 | Henry et al. |
| 3,951,980 | A | 4/1976 | Henry et al. |
| 6,127,362 | A | 10/2000 | Cignarella et al. |
| 6,462,193 | B1 | 10/2002 | Wong et al. |
| 6,531,468 | B2 | 3/2003 | Fliri et al. |
| 2007/0225492 | A1* | 9/2007 | Pinna .................. C07D 487/08 540/347 |
| 2009/0326221 | A1 | 12/2009 | Bjore et al. |
| 2010/0160626 | A1 | 6/2010 | Anderson et al. |
| 2015/0197533 | A1* | 7/2015 | Hartman ............... C07F 9/6527 424/85.5 |

FOREIGN PATENT DOCUMENTS

| NL | 6400946 A | 8/1964 | |
| WO | 1995/022526 A1 | 8/1995 | |
| WO | 1996/001262 A1 | 1/1996 | |
| WO | 1998/047902 A1 | 10/1998 | |
| WO | 1992/012155 A1 | 7/1999 | |
| WO | 2000/044755 A1 | 8/2000 | |
| WO | WO 2000044755 * | 8/2000 | ........... C07D 487/08 |
| WO | 2002/032901 A2 | 4/2002 | |
| WO | 2005/063767 A2 | 7/2005 | |
| WO | 2005/108402 A1 | 11/2005 | |
| WO | 2006/137769 A1 | 12/2006 | |
| WO | 2012/125518 A1 | 9/2012 | |
| WO | 2013/050938 A1 | 4/2013 | |

OTHER PUBLICATIONS

Cignarella, G.; Nathansohn, G. Bicyclic Homologs of Piperazine. Synthesis of 8-Methyl-3,8-diazabicyclooctanes. I. J. Org. Chem. 1961, 26(5), 1500-1504.
Schipper, E.; Boehme, W. Notes—A Novel Ring System: 3,8-Diazabicyclo[3.2.1]octane. J. Org. Chem. 1961, 26(9), 3599-3602.
Cignarella, G.; Nathansohn, G.; Occelli, G. Bicyclic Homologs of Piperazine. II. Synthesis of 3,8-Diazabicyclo[3.2.1]octane. New Synthesis of 8-Methyl-3,8-diazabicyclo[3.2.1]octane. J. Org. Chem. 1961, 26(8), 2747-2750.
Blackman, S. W.; Baltly, R. The Synthesis of 3,8-Diazabicyclo[3.2.1]octane and Some of Its N-Substituted Derivatives. J. Org. Chem. 1961, 26(8), 2750-2755.
Sturm, P. A.; Henry, D. W.; Thompson, P. E.; Zeigler, J. B.; McCall, J. W. Antifilarial Agents. Diazabicyclooctanes and Diazabicycloheptanes as Bridged Analogs of Diethylcarbamazine. J. Med. Chem. 1974, 17(5), 481-487.
Smith, S. C.; Bentley, P. D. Tandem Cyclisation and [2,3]-Stevens Rearrangement to 2-Substituted Pyrrolidines. Tetrahedron Lett., 2002, 43(5), 899-902.
Liu, H.; Cheng, T.-M.; Zhang, H.-M.; Li, R.-T. Synthesis and Structure-Activity Relationship of Di-(3, 8-diazabicyclo[3.2.1]octane) Diquaternary Ammonium Salts as Unique Analgesics. Arch. Pharm. 2003, 336(11), 510-513.
Barlocco, D.; Cignarella, G.; Tondi, D.; Vianello, P.; Villa, S.; Bartolini, A.; Ghelardini, C.; Galeotti, N.; Anderson, D. J.; Kuntzweiler, T. A.; Colombo, D.; Toma, L. Mono- an d Disubstituted-3,8-diazabicyclo[3.2.1]octane Derivatives as Analgesics Structurally Related to Epibatidine:Synthesis, Activity, and Modeling. J. Med. Chem. 1998, 41(5), 674-681.
Jain, S.; Sujatha, K.; Rama Krishna, K. V.; Roy, R.; Singh, J.; Anand, N. Lactam & Amide Acetals XXI. Use of Pyroglutamic Acid and Proline in Chiral Synthesis of Conformationally Constrained Piperazinones. Tetrahedron 1992, 48(23), 4985-4998.

(Continued)

Primary Examiner — Nizal S Chandrakumar

(57) ABSTRACT

A method of synthesizing a heteropolycycle, the method involving: reacting a bisepoxide with a first heteroatom nucleophile, to obtain a mixture comprising a diol compound; and further processing, to obtain the heteropolycycle with at least two heteroatoms within its polycyclic backbone, wherein each nitrogen within the polycyclic backbone of the heteropolycycle is introduced into the polycyclic backbone via an amine nucleophile.

19 Claims, No Drawings

(56) References Cited

OTHER PUBLICATIONS

Leuchs, H.; Guia, M.; Brewster, J. F. Versuche in der C5-Reihe: 1. Darstellung von Äther-Lactonen and Butylenoxyd-carbonsäureestern. 2. Neue Fälle von Konfigurationsänderung nach Art der Waldeschen Umkehrung bei inaktiven Verbindungen mit mehreren asymmetrischen Kohlenstoffatomen. Chem. Ber. 1912, 45, 1960-1969.

Gaudry, R.; Godin, C. New Syntheses of Hydroxyproline. J. Am. Chem. Soc. 1954, 76(1), 139-143.

Eguchi, Ch.; Kakuta, A. The Novel Synthesis of L-Hydroxyproline from D-Glutamic Acid. Bull. Chem. Soc. Jpn. 1974, 47(7), 1704-1708.

Jordis, U.; Sauter, F.; Siddiqi, S. M.; Kueenburg, B.; Bhattacharya, K. Synthesis of (1R,4R)- and (1S,4S)-2,5-Diazabicyclo[2.2.1]heptanes and Their N-Substituted Derivatives. Synthesis 1990, 10, 925-930.

Kimura, R.; Nagano T.; Kinoshita, H. A New Synthetic Method for the Preparation of α,β-Didehydroamino Acid Derivatives by Means of a Wittig-Type Reaction. Syntheses of (2S, 4S)- and (2R, 4R)-4-Hydroxyprolines. Bull. Chem. Soc. Jpn. 2002, 75, 2517-2525.

Bouzard, D.; Di Cesare, P.; Essiz, M.; Jacquet, J. P.; Kiechel, J. R.; Remuzon, P.; Weber, A.; Oki, T.; Masuyoshi, M. Fluoronaphthyridines and Quinolones as Antibacterial Agents. 2. Synthesis and Structureactivity Relationships of New 1-tert-Butyl 7-Substituted Derivatives. J. Med. Chem. 1990, 33(5), 1344-1352.

Braish, T. F.; Fox, D. E. Synthesis of (S,S)- and (R,R)-2-Alkyl-2,5-diazabicyclo[2.2.1]heptanes. J. Org. Chem. 1990, 65(5), 1684-1687.

Remuzon, P.; Bouzard, D.; Guiol, C.; Jacquet, J. P. Fluoronaphthyridines as Antibacterial Agents. 6. Synthesis and Structure-activity Relationships of New Chiral 7-(1-, 3-, 4-, and 6-Methyl-2,5-diazabicyclo[2.2.1] heptan-2-yl)naphthyridine Analogs of 7-[(1R,4R)-2,5-Diazabicyclo[2.2.1]heptan-2-yl]-1-(1,1-dimethylethyl)-6-fluoro-1,4-dihydro-4-oxo-1,8-naphthyridine-3-Carboxylic Acid. Influence of the Configuration on Blood Pressure in Dogs. A Quinolone-class Effect. J. Med. Chem. 1992, 35(15), 2898-2909.

Garner, P.; Sunithaa, K.; Shanthilal, T. An approach to the 3,8-diazabicyclo[3.2.1]octane moiety of naphthyridinomycin and quinocarcin via 1,3-dipolar cycloaddition of photochemically generated azomethine ylides. Tetrahedron Lett. 1988, 29(29), 3525-3528.

Garner, P.; Ho, W. B.; Grandhee, S. K.; Youngs, W. J.; Kennedy, V. O. Development of an Asymmetric Approach to the 3,8-Diazabicyclo[3.2.1]octane Moiety of Quinocarcin Via Intramolecular 1,3-Dipolar Cycloadditions of Photochemically Generated Azomethine Ylides. J. Am. Chem. Soc. 1985, 107(6), 1768-1769.

Garner, P.; Ho, W. B.; Shin, H. Asymmetric Synthesis of (−)-Quinocarcin. J. Am. Chem. Soc. 1992, 114(7), 2767-2768.

Oida, S.; Ohki, E. Synthesis of 3,4-Epiminopyrrolidine and 4,5-Epiminotetrahydro-1,2-oxazole. Chem. Pharm. Bull. 1968, 16(8), 1637-1639.

Oida, S.; Ohki, E. Syntheses of 3,4-Epoxy- and 3,4-Epiminopyrrolidines. Chem. Pharm. Bull. 1969, 17(5), 980-986.

Oida, S.; Kuwano, H.; Ohashi, Y.; Ohki, E. Conformational Study of 3,4-Epiminopyrrolidines in Solution. Chem. Pharm. Bull. 1970, 18(12), 2478-2488.

Meyers, A. I.; Warmus, J. S.; Dilley, G. J. 3-Pyrroline. Org. Synth. 1996, 73, 246.

Scheiner, P. Triazoline Photodecomposition: The Preparation of Aziridines. Tetrahedron 1968, 24(6), 2757-2765.

Akhtar, M. H.; Begleiter, A.; Johnson, D.; Lown, J. W.; Mclaughlin, L; Sim, S.-K. Studies Related to Antitumor Antibiotics. Part VI. Correlation of Covalent Cross-linking of DNA by Bifunctional Aziridinoquinones with their Antineoplastic Activity. Can. J. Chem. 1975, 53(19), 2891-2905.

Loriga, G.; Manca, I.; Murineddu, G.; Chelucci, G.; Villa, S.; Gessi, S.; Toma, L.; Cignarella, G.; Pinna, G. A. Synthesis of 3,6-Diazabicyclo[3.1.1]heptanes as Novel Ligands for the Opioid Receptors. Bioorg. Med. Chem. 2006, 14(3), 676-691.

Newman, H. The Preparation of 2,5-Diazabicyclo[2.2.2]octane: A Bridged Piperazine. J. Heterocycl. Chem. 1974, 11, 449-451.

Vianello, P.; Albinati, A.; Pinna, G. A.; Lavecchia, A.; Marinelli, L.; Borea, P. A.; Gessi, S.; Fadda, P. Tronci, S.; Cignarella, G. Synthesis, Molecular Modeling, and Opioid Receptor Affinity of 9,10-Diazatricyclo[4.2.1.1]decanes and 2,7-Diazatricyclo[4.4.0.0]decanes Structurally Related to 3,8-Diazabicyclo[3.2.1]octanes. J. Med. Chem. 2000, 43, 2115-2123.

Eastwood, F. W.; Gunawardana, D.; Wernert, G. T. Lithiation of Bridgehead Positions in 3,6-Bridged Piperazine-2,5-diones. Aust. J. Chem. 1982, 35(11), 2289-2298.

Ducep, J. B.; Heintzelmann, B.; Jund, K.; Lesur, B.; Schleimer, M.; Zimmermann, P. R. Synthesis of (2S,5S)-5-Fluoromethylornithine; A Potent Inhibitor of Ornithine Aminotransferase. Tetrahedron: Asymmetry 1997, 8(2), 327-335.

Al-Obedi, F. A.; Micheli, B. J. M.; Barfield, M.; Padias, A. B.; Wei, Y.; Hall, Jr., H. K. Synthesis and NMR Studies of Activated Derivatives of cis- and trans-5-Amino-6-oxopiperidine-2-carboxylic Acid and the Corresponding Bicyclic Dilactam 2,5-DBO: Potential Building Blocks for Stereoregular Polyamides and Peptides. Macromolecules, 1999, 32(20), 6507-6516.

Kemp, D. S.; McNamara, P. E. J. Org. Chem. 1984, 49(12), 2286-2288.

Kostyanovsky, R. G.; El'Natanov, Y. I.; Krutius, O. N.; Chervinn, I. I.; Lyssenko, K. A. α,α'-Diamino-α,α'-dicarboxyadipic acid tetraester: Synthesis, Lactamisation and Dilactam Structure. Mendeleev Commun. 1998, 8, 228-230.

Lyssenko, K. A.; Lenev, D. A.; Kostyanovsky, R. G. Self-assembly of Cage Structures. Paper 12: The Synthesis and Crystal Structures of 2,5-Diazabicyclo[2.2.2]octane-3,6-dione-1,4-dicarboxylic Acids and Their Diesters. Tetrahedron, 2002, 58(42), 8525-8537.

Michel, P.; Rassat, A. An Easy Access to 2,6-Dihydroxy-9-azabicyclo[3.3.1]nonane, a Versatile Synthon. J. Org. Chem. 2000, 65, 2572-2573.

Bielunas, V.; Rackauskaite, D.; Orentas, E.; Stoncius, S. Synthesis, Entiomer Separation, and Absolute Configuration of 2,6-Oxygenated 9-Azabicyclo[3.3.1]nonanes. J. Org. Chem. 2013, 78, 5339-5348.

Sarabia F.; Martin-Ortiz, L.; Lopez-Herrera, F. J. A Convergent Synthetic Approach to the Nucleoside-Type Liposidomycin Antibiotics. Org. Lett. 2003, 5(21), 3927-3930.

Concellon; J. M.; Rivero, I. A.; Rodriguez-Solla, H.; Concellon, C.; Espana, E.; Gargica-Granda, S.; Diaz, M. R. Totally Selective Synthesis of Enantiopure (3S,5R)-4-Amino-3,5-dihydroxypiperidines from Aminodiepoxides Derived from Serine. J. Org. Chem. 2008, 73(15), 6048-6051.

Breuning, M.; Steiner, M.; Mehler, C.; Paasche, A.; Hein, D. A Flexible Route to Chiral 2-endo-Substituted 9-Oxabispidines and Their Application in the Enantioselective Oxidation of Secondary Alcohols. J. Org. Chem. 2009, 74(3), 1407-1410.

Orwig, S. D.; Tan, Y. L.; Grimster, N. P.; Yu, Z.; Powers, E. T.; Kelly, J. W.; Liebermann, R. L. Binding of 3,4,5,6-Tetrahydroxyazepanes to the Acid-β-glucosidase Active Site: Implications for Pharmacological Chaperone Design for Gaucher Disease. Biochemistry 2011, 50, 10647-10657.

Paul, R.; Tchelitcheff, S. Diethylenic hydrocarbons: II. Synthesis of 3,5-dihydroxy-1-substituted piperidines from 1,4-pentadiene. Bull. Soc. Chim. France 1948, 10, 896-900.

Shainyan, B. A.; Moskalik, M. Y.; Astakhova, V. V.; Schilde, U. Novel design of 3,8-diazabicyclo[3.2.1] octane framework in oxidative sulfonamidation of 1,5-hexadiene. Tetrahedron 2014, 70, 4547-4551.

Grenning, A. J.; Snyder, J. K.; Porco, Jr., J. A. Org. Lett. 2014, 16, 792-795.

Pinna, G. A.; Cignarella, G.; Ruiu, S.; Loriga, G.; Murineddu, G.; Villa, S.; Grella, G. E.; Cossud, G.; and Fratta, W. Synthesis of Novel Diazatricyclodecanes (DTDs). Effects of Structural Variation at the C3' Allyl End and at the Phenyl Ring of the Cinnamyl Chain on μ-Receptor Affinity and Opioid Antinociception. Bioorg. & Med. Chem. 2003, 11, 4015-4026.

Hamblett, C. L.; Methot, J. L.; Mempreian, D. M.; Sloman, D. L.; Stanton, M. G.; Kral, A. M; Fleming, J. C.; Cruz, J. C.; Chenard, M.; Ozerova, N.; Hitz, A. M.; Wang, H.; Deshmukh, S. V.; Nazef, N.;

(56) References Cited

OTHER PUBLICATIONS

Harsch, A.; Hughes, B.; Dahlberg, W. K.; Szewczak, A. A.; Middleton, R. E.; Mosley, R. T.; Secrist, J. P.; and Miller, T. A. The discovery of 6-amino nicotinamides as potent and selective histone deacetylase inhibitors. Bioorg. & Med. Chem. Lett. 2007, 17, 5300-5309.

* cited by examiner

METHODS OF PRODUCING HETEROPOLYCYCLES VIA BIS-EPOXIDATION

CROSS-REFERENCE TO RELATED APPLICATIONS

This application is a national stage entry of PCT/US2015/053066, filed Sep. 30, 2015, and published as WO 2016/054123 A1 on Apr. 7, 2016, claims priority to U.S. provisional application Ser. No. 62/057,939, filed Sep. 30, 2014, which is incorporated in its entirety herein. This application is also related to U.S. Pat. No. 9,937,172, filed on Nov. 9, 2015, as a U.S. bypass continuation of Ser. No. 14/935,470, and published as US 2016/0158229 A1.

FIELD OF THE INVENTION

The invention relates to heteropolycyclic, particularly diaza- and oxaza-polycyclic, organic compounds and methods of preparing such compounds.

BACKGROUND OF THE INVENTION

Piperazine and morpholine-like compounds are relevant in the chemical industry, particularly the pharmaceutical industry, and are building blocks or components for a number of pharmacologically active substances, particularly in enhancing the bioavailability and/or antagonistic adhesion of pharmaceuticals.

Piperazine itself can be produced as one of the products in the reaction of 1,2-dichloroethane or ethanolamine with ammonia, whereby piperazine is separated from the product streams, possibly containing ethylenediamine, diethylenetriamine, and other related linear and cyclic analogs. Piperazine is consequently inexpensive relative to its bridged analogs. Likewise, morpholine may be produced by the dehydration of diethanolamine with sulfuric acid, and is similarly inexpensive due to the scalability of its industrial synthesis.

Bridged analogs of morpholine and piperazine are very interesting alternatives to their unbridged analogs, particularly for their case of exchange with piperazine and/or morpholine, and because such bridged species, due to their restrained degrees of freedom and translation, may provide more efficiently binding products upon such substitution of the non-bridged analog for the bridged. However, most known routes to these bridged analogs of piperazine, morpholine, and other heteropolycycles are not commercially viable due to the high costs from any of extensive synthetic steps, complicated and numerous separations, and high material and equipment outlays of the known alternative processes.

Numerous academic and industrial research groups have pursued new or improved methods for synthesizing such compounds, particularly methods which are scalable. Amongst a number of useful and relevant bridged analogs of piperazine are 3,8-diazabicyclo[3.2.1]octanes, 2,5-diazabicyclo[2.2.1]heptanes, 3,6-diazabicyclo[3.1.0]hexanes,

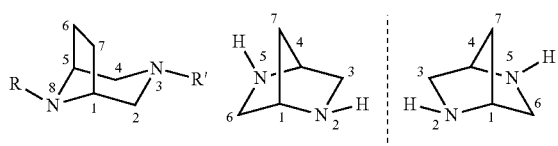

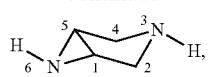

3,6-diazabicyclo[3.1.1]heptane, and 2,5-diazabicyclo[2.2.2]octanes,

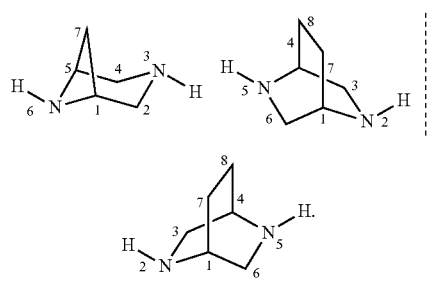

Based on the numerous known syntheses discussed in the literature, summarized in U.S. Appl. Ser. No. 62/057,939, it is clear that there is a need for alternate synthetic approaches to heteropolycycles, which may employ cheaper starting materials and/or reduce the overall steps to the end product.

A legalistic search into whether and how the scope of the inventions reported herein could be affected by publications imputed by international patent laws to be known to those of ordinary skill in the art (although such publications were not known to the inventors, nor impacted the formative thinking of the invention), revealed certain publications which warrant pre-emptive discussion.

One publication discloses the reaction of a 1:2,5:6-bisepoxyoctadiene with methylamine to form a heteromonocycle, which is subsequently acetylated with acetic anhydride. Michel, P.; Rassat, A. An Easy Access to 2,6-Dihydroxy-9-azabicyclo[3.3.1]nonane, a Versatile Synthon. J. Org. Chem. 2000, 65, 2572-2573. Michel produces only a polycycle having a single heteroatom, nitrogen, integrated into the polycyclic backbone (skeleton), and is silent on modifying the products to have even two heteroatoms in the ring backbone, instead seeking to produce, inter alia, nitroxide biradicals. Another reference of this type discloses the formation of heteropolycycle by the reaction of a 1:2,5:6-bisepoxyoctadiene with an alkylamine, but fails to disclose or suggest the formation of a heteropolycycle having more than one heteroatom, instead limiting its disclosure to the complicated enantiomers and spectroscopic properties of the 9-azabicyclo[3.3.1]nonanes. Bieliunas, V.; Rackauskaite, D.; Orentas, E.; Stoncius, S. Synthesis, Entiomer Separation, and Absolute Configuration of 2,6-Oxygenated 9-Azabicyclo[3.3.1]nonanes. J. Org. Chem. 2013, 78, 5339-5348.

Another publication discloses the reaction of a derivative of a di-epoxidized amide form of diallylamine, as a small portion of much more complicated liposidomycin-analogs at pg. 3930 (29a:29b to 30a:30b in Scheme 4). Sarabia, F.; Martin-Ortiz, L.; Lopez-Herrera, F. J. A Convergent Synthetic Approach to the Nucleoside-Type Liposidomycin Antibiotics. Org. Lett. 2003, 5(21), 3927-3930. Not only does Sarabia not produce a polycycle, but rather only a monoheterocycle, the reaction in question would not have lent itself to further cyclization within the scope of this invention, even if such a reaction were suggested and would have been reasonably expected to function.

A further reference discloses separate reactions of a derivative of 1:2,4:5-bisepoxypentane with an alkylamine to give various dihydroxypiperidines. Concellon; J. M.; Rivero, I. A.; Rodriguez-Solla, H.; Concellon, C.; Espana, E.; Garcia-Granda, S.; Diaz, M. R. Totally Selective Synthesis of Enantiopure (3S,5 R)-4-Amino-3,5-dihydroxypiperidines from Aminodiepoxides Derived from Serine. *J. Org. Chem.* 2008, 73(15), 6048-6051. Concellon, however, does not suggest further cyclization, nor that a target product should include two or more heteroatoms in the backbone of any such heteropolycycle.

A further reference discloses a reaction of two epoxides in the ultimate formation of a heteropolycycle with two or more heteroatoms in the ring backbone. Breuning, M.; Steiner, M.; Mehler, C.; Paasche, A.; Hein, D. A Flexible Route to Chiral 2-endo-Substituted 9-Oxabispidines and Their Application in the Enantioselective Oxidation of Secondary Alcohols. *J. Org. Chem.* 2009, 74(3), 1407-1410. However, Breuning does not disclose reacting a bisepoxide, nor a single-pot reaction of two epoxides upon a single starting molecule.

Similarly, WO 2006/137769 A1 discloses the reaction of a bisepoxidated analog of diallyl amine, and ultimately forms a heteropolycycle from the heteromonocyclic diol intermediate. However, WO 2006/137769 A1 discloses only oxadiazabispidine analogs which have nitrogen heteroatoms introduced into to heteropolycyclic backbone without the use of an (amine) nucleophile, i.e., with a sulfonamide and epichlorohydrin, based on the particular reaction sequence suggested therein, e.g., at pg. 18. Bisepoxides lacking hydroxyl substituents are not disclosed or suggested by WO 2006/137769 A1, nor is the production of a heteropolycycle into which each nitrogen is introduced by an amine nucleophile. WO 2013/050938 A1 also discloses subject matter related to the reaction of an N-protected epoxidized analog of diallylamine, producing oxadiazabispidine analogs, i.e., heteropolycycles. However, WO 2013/050938 A1 likewise describes the reaction of a protected starting material, already having a nitrogen in the backbone chain. Unlike the claimed embodiments of the present invention, which introduce all of the nitrogen heteroatoms into the skeleton of the claim, WO 2013/050938 A1 discloses already introducing a nitrogen into the heteropolycycle before the reaction of the bisepoxide, see, e.g., pg. 47-48. Moreover, WO 2013/050938 A1 does not disclose or suggest a reaction which introduces all heteroatoms, or at least all nitrogen heteroatoms, into the polycyclic backbone after reacting the bisepoxide. US 2009/0326221 A1 and US 2010/0160626 A1 suffer from the same fundamental flaws. Moreover, WO 2006/137769 A1 and its kin disclose only oxygenated analogs of bispidine, and do not suggest larger or smaller rings, nor rings having 2, 4, or more heteroatoms in the heteropolycyclic backbone.

Another set of references discloses the reaction of certain sugar bisepoxides with alkylamines to obtain polyhydroxylated azepanes. Orwig, S. D.; Tan, Y. L.; Grimster, N. P.; Yu, Z.; Powers, E. T.; Kelly, J. W.; Lieberman, R. L. Binding of 3,4,5,6-Tetrahydroxyazepanes to the Acid-β-glucosidase Active Site: Implications for Pharmacological Chaperone Design for Gaucher Disease. *Biochemistry* 2011, 50, 10647-10657; WO 95/022526 A1. However, none of these iditol references provides a motivation to create a polycyclic compound from the obtained azepanes, nor any indication that such further processing would be achievable. U.S. Pat. No. 6,462,193 B1 is of similar deficient character in this regard.

A further publication discloses a reaction of a bisepoxide with a nucleophile. Paul, R.; Tchelitcheff, S. Diethylenic hydrocarbons: II. Synthesis of 3,5-dihydroxy-1-substituted piperidines from 1,4-pentadiene. *Bull. Soc. Chim. France* 1948, 10, 896-900. Paul, however, only produces a heteromonocycle, and makes no mention of polycyclic compounds. Furthermore, were the piperidine monocycles suggestive of polycycles, more than a half century has passed since Paul's publication, a substantially long period of time.

A 2014 reference discloses a method of producing 3,8-diazabicyclo[3.2.1]octane by an oxidative route from 1,5-hexadiene, but its method does not employ epoxidation and requires a sulfonamide-protected amine for the initial ring opening step. Shainyan, B. A.; Moskalik, M. Y.; Astakhova, V. V.; Schilde, U. Novel design of 3,8-diazabicyclo[3.2.1] octane framework in oxidative sulfonamidation of 1,5-hexadiene. *Tetrahedron* 2014, 70, 4547-4551.

A further 2014 reference discloses a reaction of a bisepoxide with an amine nucleophile to form a cyclic species, but the post-epoxidation reaction sequence disclosed therein does not further cyclize the product of the epoxide opening and furthermore forms a heteropolycycle having only a single heteroatom in its carbon backbone. Grenning, A. J.; Snyder, J. K.; Porco, Jr., J. A. *Org. Lett.* 2014, 16, 792-795.

BRIEF SUMMARY OF THE INVENTION

An aspect of the invention provides a method of synthesizing a heteropolycycle, the method comprising: reacting a bisepoxide with a first heteroatom nucleophile, to obtain a mixture comprising a diol compound; and further processing, to obtain the heteropolycycle comprising at least two heteroatoms within its polycyclic backbone, wherein each nitrogen within the polycyclic backbone of the heteropolycycle is preferably introduced into the polycyclic backbone via an amine nucleophile. An aspect of the invention is the synthesis of a heteropolycycle without employing a reduction, particularly without reducing a carbonyl, and preferably employing a bisepoxide but without employing an optionally N-protected bisepoxidized diallyl amine.

DETAILED DESCRIPTION OF THE INVENTION

Methods within the scope of the invention generally involve reacting a bisepoxide with a nucleophile to give an intermediate, whereby the intermediate can be optionally protected, optionally activating alcohols of the resulting intermediates with leaving groups, and again cyclized to give a heteropolycycle, wherein preferably all nitrogens, more preferably all N, O, S, and/or P heteroatoms, most preferably all heteroatoms, in the heteropolycyclic backbone are introduced via nucleophiles which are distinct molecules from the bisepoxide, preferably as the reactive nucleophilic element of the nucleophile(s). An aspect of the invention involves forming a heteropolycycle from a non-cyclic starting material or from a compound containing no non-epoxide cyclic moieties, without a reduction, particularly without a reduction of a carbonyl. The inventive process preferably avoids the use of epichlorohydrin, preferably avoids the use of a sulfonamide nucleophile.

An aspect of the invention provides a method of synthesizing a pharmaceutical compound, the method comprising: reacting, with a first heteroatom nucleophile, a bisepoxide of formula (I) or (II)

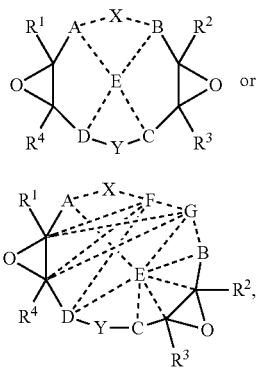

wherein a hyphenated line indicates that the bond is optionally absent, -A- is a bond, hydrogen, $(CH_2)_mC$, $C(CH_2)_m$, $(CH_2)_mC(CH_2)_n$, $CH(CH_2)_m$, $(CH_2)_mCH$, $(CH_2)_mCH(CH_2)_n$, $(CH_2)_mCH_3$, $CH_2(CH_2)_mOH$, $CH_2(CH_2)_mOR$, $CH_2(CH_2)_mSH$, $CH_2(CH_2)_mSR$, $CH_2(CH_2)_mNH_2$, $CH_2(CH_2)_mNHR$, $CH_2(CH_2)_mNR_2$, $CH_2(CH_2)_mPH_2$, $CH_2(CH_2)_mPHR$, or $CH_2(CH_2)_mPR_2$, -B- is a bond, hydrogen, $(CH_2)_oC$, $C(CH_2)_o$, $(CH_2)_oC(CH_2)p$, $CH(CH_2)_o$, $(CH_2)_oCH$, $(CH_2)_oCH(CH_2)_p$, $(CH_2)_oCH_3$, $CH_2(CH_2)_oOH$, $CH_2(CH_2)_oOR$, $CH_2(CH_2)_oSH$, $CH_2(CH_2)_oSR$, $CH_2(CH_2)_oNH_2$, $CH_2(CH_2)_oNHR$, $CH_2(CH_2)_oNR_2$, $CH_2(CH_2)_oPH_2$, $CH_2(CH_2)_oPHR$, or $CH_2(CH_2)_oPR_2$, -C- is a bond, $(CH_2)_q$, $(CH_2)_qC$, $C(CH_2)_q$, $(CH_2)_qC(CH_2)_r$, $CH(CH_2)_q$, $(CH_2)_qCH$, or $(CH_2)_qCH(CH_2)_r$, -D- is a bond, $(CH_2)_s$, $(CH_2)_sC$, $C(CH_2)_s$, $(CH_2)_sC(CH_2)_t$, $CH(CH_2)_s$, $(CH_2)_sCH$, or $(CH_2)_sCH(CH_2)_t$, -E- is absent or a bond, $(CH_2)_u$, $(CH_2)_uC$, $C(CH_2)_u$, $(CH_2)_uC(CH_2)_v$, $CH(CH_2)_u$, $(CH_2)_uCH$, $(CH_2)_uCH(CH_2)_v$, or $(CH_2)_uCH_3$, -F- is absent or a bond, hydrogen, $(CH_2)_hC$, $C(CH_2)_h$, $(CH_2)_hC(CH_2)_j$, $CH(CH_2)_h$, $(CH_2)_hCH$, $(CH_2)_hCH(CH_2)_j$, $(CH_2)_hCH_3$, $CH_2(CH_2)_hOH$, $CH_2(CH_2)_hOR$, $CH_2(CH_2)_hSH$, $CH_2(CH_2)_hSR$, $CH_2(CH_2)_hNH_2$, $CH_2(CH_2)_hNHR$, $CH_2(CH_2)_hNR_2$, $CH_2(CH_2)_hPH_2$, $CH_2(CH_2)_hPHR$, or $CH_2(CH_2)_hPR_2$, -G- is absent or a bond, hydrogen, $(CH_2)_kC$, $C(CH_2)_k$, $(CH_2)_kC(CH_2)_l$, $CH(CH_2)_k$, $(CH_2)_kCH$, $(CH_2)_kCH(CH_2)_l$, $(CH_2)_kCH_3$, $CH_2(CH_2)_kOH$, $CH_2(CH_2)_kOR$, $CH_2(CH_2)_kSH$, $CH_2(CH_2)_kSR$, $CH_2(CH_2)_kNH_2$, $CH_2(CH_2)_kNHR$, $CH_2(CH_2)_kNR_2$, $CH_2(CH_2)_kPH_2$, $CH_2(CH_2)_kPHR$, or $CH_2(CH_2)_kPR_2$, h, j, k, l, m, n, o, p, q, r, s, t, u, and v are independently 0, 1, 2, or 3, -X- is absent or is NH, O, S, or PH, and -Y- is a bond, O, S, or PH, each R is independently hydrogen or an optionally substituted methyl, ethyl, $C_3$ alkyl group, $C_4$ alkyl group, $C_5$ alkyl group, $C_2$ alkenyl group, $C_3$ alkenyl group, $C_4$ alkenyl group, $C_5$ alkenyl group, formyl, carboxylate, hydroxymethyl, acetyl, isovaleryl, or optionally substituted phenyl, wherein 1, 2, 3, or 4 hydrogens upon any alkyl group of -A-, -B-, -C-, -D-, -E-, or R (meaning, herein, that one or more hydrogens from any of -A- through R, or only one of -A- through R, and/or when R is H, optionally replacing R) is optionally replaced by an azide, amine, nitrile, isonitrile, isocyanate, thiocyanate, isothiocyanate, nitro, nitroso, thiol, thioether, fluoride, chloride, bromide, or iodide, hydroxyl, methyl, ethyl, n-propyl, isopropyl, n-butyl, iso-butyl, sec-butyl, vinyl, $C_3$ alkenyl group, $C_4$ alkenyl group, $C_5$ alkenyl group, $OCH_3$, $OCH_2CH_3$, $OCH_2CH_2CH_3$, $OCH(CH_3)_2$, $OCH_2CH_2CH_2CH_3$, isobutoxy, sec-butoxy, methoxymethyl, methoxyethyl, ethoxymethyl, (hetero)aryl ether (meaning heteroaryl or aryl), $C_1$-$C_5$ carboxylate, $C_0$-$C_5$ sulfonate, $C_1$-$C_{10}$ amide (meaning amide C(O)N or reverse amide NC(O)), $C_1$-$C_{10}$ (reverse) ester, $C_1$-$C_{10}$ (reverse) carbamate, $C_0$-$C_{10}$ (reverse) sulfonamide, $C_0$-$C_{10}$ (reverse) sulfonic ester, $C_1$-$C_6$ ketal, $C_1$-$C_5$ ketone, or $C_1$-$C_5$ aldehyde, wherein 2 to 4 hydrogens upon any alkyl group of -A-, -B-, -C-, -D-, -E-, or R are optionally removed to form an optionally substituted $C_3$-$C_{10}$ ring, wherein two hydrogens upon any alkyl group of -A-, -B-, -C-, -D-, -E-, or R are optionally removed to form a carbonyl, ketal, or an exo-$C_1$-$C_4$ alkenyl group, to obtain a mixture comprising a diol compound; and further processing, to obtain the heteropolycycle comprising at least two heteroatoms within its polycyclic backbone.

An aspect of the invention provides a method of synthesizing a pharmaceutical compound, the method comprising: reacting a bisepoxide as described herein with a heteroatom nucleophile, to obtain a mixture comprising a diol compound; further processing, to obtain the heteropolycycle; and reacting the heteropolycycle with a precursor component to the pharmaceutical compound, and, optionally, further treating a product of the reacting, to obtain the pharmaceutical compound. Preferably the method of synthesizing the pharmaceutical compound or the heteropolycycle is one wherein the further treating comprises functionalizing, e.g., acylating or alkylating, a nitrogen of the product of the reacting, and/or forming a pharmaceutically suitable salt of the product of reacting.

An aspect of the invention is the method of synthesizing a heteropolycycle, the method comprising: reacting a bisepoxide of formula (II):

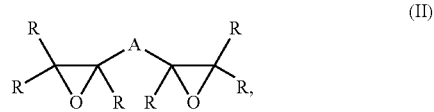

wherein -A- may be absent (i.e., 1:2,3:4-diepoxybutane analogs), or optionally substituted methylene, ethylene, propylene, $CH_2OCH_2$, $CH_2SCH_2$, $CH_2N(R)CH_2$, (R here preferably not forming a sulfonamide), $CH_2P(R)CH_2$, $CH_2OCH_2CH_2$, $CH_2SCH_2CH_2$, $CH_2N(R)CH_2CH_2$, $CH_2P(R)CH_2CH_2$, $CH_2CH_2OCH_2CH_2$, $CH_2CH_2SCH_2CH_2$, $CH_2CH_2N(R)CH_2CH_2$, $CH_2CH_2P(R)CH_2CH_2$, $CH_2OCH_2CH_2$, $CH_2SCH_2CH_2$, $CH_2N(R)CH_2CH_2CH_2$, $CH_2P(R)CH_2CH_2CH_2$, $CH_2CH_2OCH_2CH_2CH_2$, $CH_2CH_2SCH_2CH_2CH_2$, $CH_2CH_2N(R)CH_2CH_2CH_2$, $CH_2CH_2P(R)CH_2CH_2CH_2$, wherein 1, 2, 3, 4, or 5 protons of any of the foregoing may be replaced by a substituent, two hydrogens upon any alkyl group of -A- and/or R optionally being removed to form an optionally substituted $C_3$-$C_7$ (hetero) cyclic ring, and R is independently, hydrogen, azide, amine, nitrile, isonitrile, cyanate, isocyanate, thiocyanate, isothiocyanate, nitro, nitroso, thiol, thioether, fluoride, chloride, bromide, iodide, methyl, ethyl, n-propyl, isopropyl, n-butyl, isobutyl, sec-butyl, methoxy ($OCH_3$), ethoxy ($OCH_2CH_3$), propoxy ($OCH_2CH_2CH_3$), isopropoxy ($OCH(CH_3)_2$), butoxy ($OCH_2CH_2CH_2CH_3$), isobutoxy, sec-butoxy, cyano, methoxymethyl, methoxyethyl, ethoxymethyl, hydroxy, $C_1$-$C_4$ carboxylate (reverse), $C_0$-$C_4$ sulfonate, $C_1$-$C_4$ (reverse) amide, $C_1$-$C_4$ (reverse) ester, $C_1$-$C_4$ (reverse) carbamate, $C_1$-$C_4$ (reverse) sulfonamide, $C_1$-$C_4$ ketone, or $C_1$-$C_4$ aldehyde, with a nucleophile; and further processing, to obtain the heteropolycycle. In this application, "reverse" in the context of, e.g., carbonyl compounds, means $-CH_2OC(O)CH_2-$, rather than $-CH_2C(O)OCH_2-$.

A preferred embodiment of the invention produces a heteropolycycle comprising 2,5-diazabicyclo[2.2.2]octane(s), in some circumstances, both 2,5-diazabicyclo[2.2.2]octane(s) and 3,8-diazabicyclo[3.2.1]octane(s). This approach may, in some embodiments, preferably produce primarily, i.e., 75%, 85%, 90%, 95%, 99%, or only a 2,5-diazabicyclo[2.2.2]octane. Alternatively, this approach may, in some embodiments, preferably produce primarily, i.e., 75%, 85%, 90%, 95%, 99%, or only a 3,8-diazabicyclo[3.2.1]octane. A further embodiment in this approach may produce anywhere in the ranges 1:1, 1:2, 2:3, 1:3, 3:2, 3:1, 1:4, and/or 4:1 of a mixture of products, 2,5-diazabicyclo[2.2.2]octane(s) and 3,8-diazabicyclo[3.2.1]octane(s). Such an embodiment may proceed, e.g., from 1,5-hexadiene, or the bisepoxide thereof.

A preferred embodiment of the invention produces 2,5-diazabicyclo[2.2.1]heptane(s) and 3,6-diazabicyclo[3.1.1]heptane(s), more preferably, 3,6-diazabicyclo[3.1.1]heptane(s). This approach may, in some embodiments, preferably produce primarily, i.e., 75%, 85%, 90%, 95%, 99%, or only a 3,6-diazabicyclo[3.1.1]heptane. Such an embodiment may proceed, e.g., from 1,4-pentadiene, or the bisepoxide thereof.

A preferred embodiment of the invention produces 3,6-diazabicyclo[3.1.0]hexane(s) and 2,5-diazabicyclo[2.2.0]hexane(s), more preferably, 3,6-diazabicyclo[3.1.0]hexane(s). This approach may, in some embodiments, preferably produce primarily, i.e., 75%, 85%, 90%, 95%, 99%, or only a 3,6-diazabicyclo[3.1.0]hexane(s). Such an embodiment may proceed, e.g., from 1,3-butadiene, or the bisepoxide thereof.

In a particularly preferred embodiment of the invention, the bisepoxide comprises 1:2,3:4-bisepoxybutane, 1:2,4:5-bisepoxypentane, 1:2,5:6-bisepoxyhexane, or 1:2,6:7-bisepoxyheptane, most preferably 1:2,5:6-bisepoxyhexane. Any of these bisepoxides is preferably used individually, i.e., not as a mixture of homologs. Preferable embodiments may employ stereospecific epoxidizing methods known in the art (e.g., Sharpless, Shi, Jacobsen-Katsuki, etc.) to use particular stereochemically enriched or pure enantiomers or diastereomers of the bisepoxide. A preferred embodiment includes producing a nonracemic heteropolycycle by, e.g., optically resolving the racemic product mixture with a nonracemic acid, through repeated recrystallization of the formed salts from a suitable solvent, or via asymmetric synthesis, by employing a nonracemic nucleophile, such as a naturally occurring and/or stereopure nucleophile. The purity of the bisepoxide can be any that does not hinder facile separation. The purity of the bisepoxide is preferably at least 90%, but may be any level of purity reaching the limits of HPLC detection. The stereopurity of an enriched bisepoxide, or isolated heteropolycycle may be, for example, at least 60, 70, 75, 80, 85, 90, 95, 96, 97, 97.5, 98, 98.5, 99, 99.5, 99.9, or 99.99 e.e., up to the limits of detection.

The inventive method is preferably one wherein the further processing comprises displacing the leaving group-activated hydroxyl group with a second heteroatom-comprising nucleophile to form a raw mixture comprising the heteropolycycle. The method may further comprise purifying the raw mixture to obtain a purified mixture which is enriched of the heteropolycycle relative to the raw mixture. In fact, at any step of the reaction, the product mixtures may be purified, which may include, for example, separating diastereomers from each other and/or a chiral separation. The method of the invention preferably produces single racemates. However, in certain embodiments, it could be preferably not to separate intermediates until the final heteropolycycle (preferably, bicyclic or tricyclic, most preferably bicyclic). In such an embodiment, the method preferably involves a further processing comprising separating two different heteropolycycles in the raw mixture from each other, wherein the two different heteropolycycles respectively have a different bonding arrangement of a bridging portion of each heteropolycycle.

After the bisepoxidation, certain embodiments of the invention employ an amine or phosphine to open the epoxides and form a ring. This approach generally produces a diol, which may be reacted, optionally with protection of the amine or phosphine, to generate two leaving groups out of the hydroxides. Examples of such leaving groups are tosylates, sulfates, optionally substituted phenylsulfonates, mesylates, trifluoroacetates, triflates, nosylates, chlorides, bromides, iodides, and triphenylphosphineoxides. Inventive embodiments comprising activating at least one hydroxyl group of the diol compound with a leaving group forming compound, thereby converting the hydroxyl group into a better leaving group relative to the hydroxyl group, and obtaining an intermediate comprising a leaving group-activated hydroxyl group, may involve contacting at least two, only two, at least three, only three, etc., hydroxyl groups of the diol compound with the leaving group forming compound, to obtain the intermediate comprising two leaving-group activated hydroxyl groups.

A bicyclizable diastereomer of 5(S)-hydroxy-2(R)-piperidinemethanol and its enantiomer are seen in Scheme 11.

Scheme 11: Stereochemical factors in bicyclization.

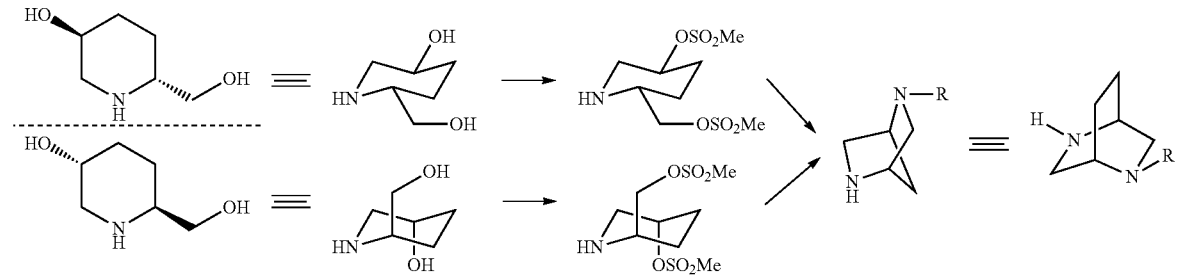

The diastereomeric outcome of the epoxide opening, in embodiments in which no stereopure bisepoxide is used, or a bisepoxide is used wherein the desired diastereomers are present in the form of a racemate of desired enantiomers, may provide 2R,5R and 2S,5S enantiomers and the diastereomeric meso compound in the case of 1:2,5:6-bisepoxyhexane. The 2R,5R and 2S,5S enantiomers cannot bicyclize in a reaction proceeding under S$_N$2 conditions. Only the meso compound bicyclizes under S$_N$2 conditions, as in Scheme 12.

Scheme 12: Predicted cyclizations of 2R,5R,2S,5S (above) and meso (below) bisepoxyhexanes.

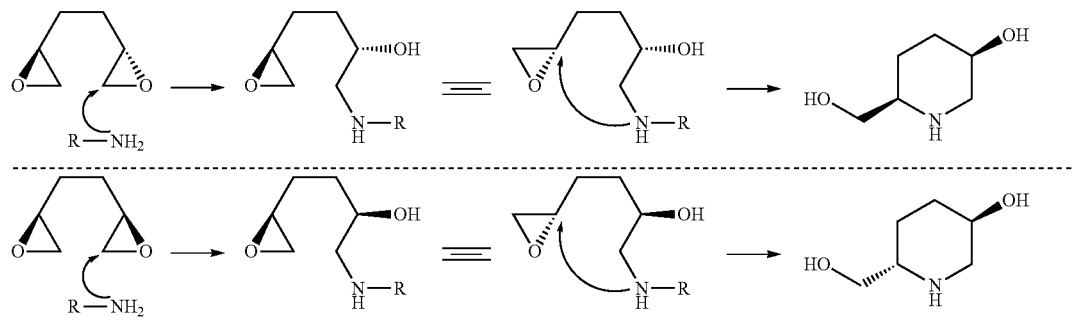

Suitable starting materials for the bisepoxide include essentially any diene, such as butadiene, 1,4-pentadiene, 1,3-pentadiene, 1,5-hexadiene, 1,4-hexadiene, 1,3-hexadiene, 2,4-hexadiene, 1,6-heptadiene, 1,5-heptadiene, 1,4-heptadiene, 2,5-heptadiene, 3,5-heptadiene, 1,7-octadiene, 1,6-octadiene, 2,6-octadiene, 2,5-octadiene, 1,5-octadiene, 2,4-octadiene, cyclopentadiene, 1,3-cyclohexadiene, 1,4-cyclohexadiene, 1,4-oxazine, 1,4-dioxin, norbornadiene, dicyclopentadiene, 4-vinylcyclohexene, 3-vinylcyclohexene, 1-vinylcyclohexene, i.e., any vinylcyclohexene, hepta-2,6-dienoic acid, 1,2-divinylbenzene or other substituted arene or heteroarene carrying two or more unsaturations in sidechains on adjacent positions of the aryl core, i.e., ortho to one another (e.g., benzene, naphthalene, pyridine, pyrazine, purine, indolizine, quinolizine, pyridazine, imidazole, indole, isoindole, naphthyridine, quinoline, isoquinoline, pyrrole, furan, thiophene, phosphole, borole, arsole, stibole, silole, bismole, pyrazole, oxazole, isoxazole, thiazole, isothiazole, oxazines, carbazole and other benzo-fused and/or partially hydrogenated analogs of these, etc.), a saturated cyclic compound having approx. 2-5 carbon-carbon bond distance (for example, 1-4 atomic) spaced alkenyl substituents (e.g., 1,1-divinylcyclopropane, 1,2-divinylcyclopropane, 1,1-divinylcyclobutane, 1,2-divinylcyclobutane, 1,3-divinylcyclobutane, 1,1-divinylcyclopentane, 1,2-divinylcyclopentane, 1,3-divinylcyclopentane, 1,1-divinylcyclohexane, 1,2-divinylcyclohexane, 1,3-divinylcyclohexane, 1,4-divinylcyclohexane, 1,1-divinylcycloheptane, 1,2-divinylcycloheptane, 1,3-divinylcycloheptane, 1,4-divinylcycloheptane, 1,2-divinylaziridine, 2,2-divinylaziridine, 2,3-divinylaziridine, 2,2-divinyloxirane, 2,3-divinyloxirane, 2,2-divinylthiirane, 2,3-divinylthiirane, 2,2-divinyloxetane, 2,3-divinyloxetane, 3,3-divinyloxetane, 2,4-divinyloxetane, 1,2-divinylazetidine, 2,2-divinylazetidine, 1,3-divinylazetidine, 2,3-divinylazetidine, 3,3-divinylazetidine, 2,4-divinylazetidine, 2,2-divinylthietane, 2,3-divinylthietane, 3,3-divinylthietane, 2,4-divinylthietane, 1,2-divinylpyrrolidine, 2,2-divinylpyrrolidine, 1,3-divinylpyrrolidine, 2,3-divinylpyrrolidine, 3,3-divinylpyrrolidine, 2,4-divinylpyrrolidine, 3,4-divinylpyrrolidine, 2,5-divinylpyrrolidine, 2,2-divinyltetrahydrofuran, 2,3-divinyltetrahydrofuran, 3,3-divinyltetrahydrofuran, 2,4-divinyltetrahydrofuran, 3,4-divinyltetrahydrofuran, 2,5-divinyltetrahydrofuran, 2,2-divinylphospholane, 2,3-divinylphospholane, 3,3-divinylphospholane, 2,4-divinylphospholane, 3,4-divinylphospholane, 2,5-divinylphospholane, 2,2-divinylthiolane, 2,3-divinylthiolane, 3,3-divinylthiolane, 2,4-divinylthiolane, 3,4-divinylthiolane, 2,5-divinylthiolane, 1,2-divinylpiperidine, 2,2-divinylpiperidine, 1,3-divinylpiperidine, 2,3-divinylpiperidine, 3,3-divinylpiperidine, 1,4-divinylpiperidine, 2,4-divinylpiperidine, 3,4-divinylpiperidine, 4,4-divinylpiperidine, 2,5-divinylpiperidine, 3,5-divinylpiperidine, 2,6-divinylpiperidine, 1,2-divinylpiperazine, 2,2-divinylpiperazine, 1,3-divinylpiperazine, 2,3-divinylpiperazine, 1,4-divinylpiperazine, 2,5-divinylpiperazine, 2,6-divinylpiperazine, 2,2-divinylmorpholine, 2,3-divinylmorpholine, 3,3-divinylmorpholine, 2,4-divinylmorpholine, 3,4-divinylmorpholine, 2,5-divinylmorpholine, 3,5-divinylmorpholine, 2,6-divinylmorpholine, etc., as well as allyl-vinyl and diallyl analogs of these), cyclohexa-1,4-diene-1-carboxylic acid, cyclohexa-2,5-diene-1-carboxylic acid, diallyl ether, muurolenes, germacradienes, germacradienols, curcumin, demethoxycurcumin, bisdemethoxycurcumin, velleral, valencene, capsidiol, bisabolols, aristolochene, amorpha-4,11-diene, eremophilene, gurjurene, bergamotenes, lavandulol, himachalenes, amorphenes, safranates, safranal, perillaldeyhde, perillalcohol, carveol, carvones, elemol, jasmolone, nootkatone, tagetone, solanone, vetivones, santalols, lindestrene, abietic acid, artemisinic acid, caryophyllenes, cadinenes, guaienes, irones, selinenes, damascones, ionones, isolimonene, dipentene, terpinenes, phellandrenes, linalool, nerol, piperine, chavicine, farnesol, myrcene, ocimene, damascenones, gurjurenes, eremophilene, curzerenone, pyrethrolone, vetivones, sesquiphellandrenes, cadinenes, zingiberene, parthenin, santonin, geraniol, limonene, bisabolenes, citral, jasmone, cannabidiol, valerenic acid, nerolidol, geranic acids, etc. Substituted analogs (e.g., the alkyl, (hetero)aryl, (hetero)cyclic, allyl, and/or vinyl moiety having 1, 2, or 3 substituents) and/or protected analogs (e.g., in amide, carbamate, ester, ether, alkyl, silyl, etc., form) of any of these, as relevant, are also within the scope of the invention.

Suitable oxidizing agents to produce bisepoxides useful in the inventive method include any of those known to persons of ordinary skill in the art, such as various peroxides, e.g., hydrogen peroxide, peracetic acid, OXONE®, m-chloroperbenzoic acid (MCPBA), and tert-butyl hydroperoxide. These and any further suitable epoxidizing agent known to those of ordinary skill in the art can be used to produce a bisepoxide within the scope of the invention, i.e., an organic compound having at least two, and preferably only two, epoxide moieties.

A nucleophile useful for the present invention is any one capable of forming a ring upon reaction with two epoxides upon a single molecule. The nucleophile preferably comprises a heteroatom, particularly N, O, S, or P, and the heteroatom preferably works as the nucleophilic element. The nucleophile is preferably an amine (including ammonia), a phosphine (including $PH_3$), hydrogen sulfide, $HS^-$, $HO^-$, or water. Preferred nucleophiles include ammonia, primary amines, amino acids, alkylamines (e.g., methylamine, ethylamine, isopropylamine, propylamine, etc.), arylamines (e.g., aniline), and arylalkylamines (e.g., benzylamine, racemic, R, or S-analogs of α-alkylbenzylamines, etc.) including a saturated or unsaturated, bicyclic or tricyclic fused hydrocarbon group which may be substituted, or a saturated or unsaturated, bicyclic, or tricyclic fused heterocyclic group which may be substituted. Particularly preferred nucleophiles include ammonia, methylamine, ethylamine, optionally substituted benzylamine, optionally substituted 2-phenylethylamine, optionally substituted 1-phenylethylamine (racemic, R, or S), optionally substituted aniline, hydrazine, and 1,2-ethylenediamine. Any nucleophile having two or more reactive moieties may be protected. Most preferred nucleophiles are presently considered to be ammonia or benzylamine. Isotopically enriched nucleophiles, and/or bisepoxides, are also contemplated, e.g., those comprising enriched isotopes, such as $^2H$, $^3H$, $^{13}C$, $^{14}C$, $^{15}N$, $^{18}O$, $^{32}P$, and/or $^{33}P$.

A heteropolycycle within the scope of the invention may contain 2, 3, 4, or 5 rings, more preferably being bicyclic, tricyclic, or tetracyclic, most preferably being bicyclic. Within the meaning of the invention, a heteroatom is not a carbon atom and not a hydrogen atom, and is preferably an atom having at least two covalent bonding sites, more preferably O, N, S, P, and/or Sc, most preferably N and/or O. Moreover, a heteropolycycle according to the invention preferably contains two or more heteroatoms interrupting the carbon backbone of the ring(s), including nitrogen, oxygen, sulfur, and/or phosphorus, more preferably 2, 3, 4, or 5 of such heteroatoms, most preferably 2 or 3 such heteroatoms, particularly preferably 2 heteroatoms. Each heteroatom in the heteropolycycle may be nitrogen, or each heteroatom in the heteropolycycle may be oxygen, or the heteroatoms may be a mixture of nitrogen, sulfur, phosphorus, and/or oxygen, or the heteroatoms may be a mixture of nitrogen and oxygen. The heteropolycycle preferably has at least one (e.g., 1, 2, or 3) heteroatom capable of bonding to three or more atoms and preferably contains at least one nitrogen and/or oxygen, most preferably one or two nitrogens or only two nitrogens. The heteroatoms are preferably distributed in any of the contiguous rings of the polycyclic backbone, though more preferable embodiments contain all heteroatoms in the backbone of the main (or larger) ring of the polycycle.

Heteropolycycle products within the scope of the inventive method include any diazabicycle, oxazabicycle, azaphosphobicycle, oxaphosphobicycle, diazatricycle, oxazatricycle, azaphosphotricycle, oxaphosphotricycle, optionally substituted and/or fused with aliphatic or aromatic rings, insofar as the heteropolycycle contains at least two heteroatoms (e.g., N, O, S, P, and/or Se) within the backbone of the polycycle and the polycycle is at least bicyclic. Heteropolycycles obtained according to aspects of the invention preferably include one or more optionally substituted analogs of 2,5-diazabicyclo[2.2.2]octane, 3,8-diazabicyclo[3.2.1]octane, 2,5-diazabicyclo[2.2.1]heptane, 3,6-diazabicyclo[3.1.1]heptane, 3,6-diazabicyclo[3.1.0]hexane, 2,5-diazabicyclo[2.2.0]hexane, 2-aza-5-oxabicyclo[2.2.2]octane, 3-aza-8-oxabicyclo[3.2.1]octane, 2-aza-5-oxabicyclo[2.2.1]heptane, 3-aza-6-oxabicyclo[3.1.1]heptane, 3-aza-6-oxabicyclo[3.1.0]hexane, 2-aza-5-oxabicyclo[2.2.0]hexane, 2-aza-5-phosphabicyclo[2.2.0]hexane, 3-aza-6-phosphabicyclo[3.1.0]hexane, 6-aza-3-phosphabicyclo[3.1.0]hexane, 2-aza-5-phosphabicyclo[2.2.1]heptanes, 2-aza-5-phosphabicyclo[2.2.2]octane, 6-aza-3-phosphabicyclo[3.1.1]heptanes, 3-aza-6-phosphabicyclo[3.1.1]heptanes, 3-aza-8-phosphabicyclo[3.2.1]octane, 8-aza-3-phosphabicyclo[3.2.1]octane, 3-oxa-6-phosphabicyclo[3.1.0]hexane, 6-oxa-3-phosphabicyclo[3.1.0]hexane, 2-oxa-5-phosphabicyclo[2.2.0]hexane, 2-oxa-5-phosphabicyclo[2.2.1]heptanes, 2-oxa-5-phosphabicyclo[2.2.2]octane, 6-oxa-3-phosphabicyclo[3.1.1]heptanes, 3-oxa-6-phosphabicyclo[3.1.1]heptanes, 3-oxa-8-phosphabicyclo[3.2.1]octane, 8-oxa-3-phosphabicyclo[3.2.1]octane, etc.

A person of ordinary skill in the art will immediately recognize that the aliphatic carbons of the heteropolycycles, and, correspondingly, their precursors, may be substituted with a substituent including methyl, ethyl, $C_3$, $C_4$, $C_5$, or $C_6$ alkyl groups, ethers comprising 1, 2, 3, 4, 5, or 6 carbons, alkylhalides comprising 1, 2, 3, 4, 5, or 6 carbons, primary, secondary, and/or tertiary amines comprising 1, 2, 3, 4, 5, 6, 7, 8, 9, or 10 carbons, ammonium groups comprising 1, 2, 3, 4, 5, 6, 7, 8, 9, or 10 carbons, halides (fluoride, chloride, bromide, and/or iodide), nitriles, isonitriles, azides, cyanates, isocyanates, thiocyanates, isothiocyanates, nitros, nitrosyls, oximes, hydroxyls, alkyl ethers, thiols, thioethers, aryls, aryl ethers, sulfonates, acyloxy groups (optionally reversed) comprising 1, 2, 3, 4, 5, or 6 carbons, keto or aldehyde groups comprising 1, 2, 3, 4, 5, or 6 carbons, primary and/or secondary (optionally reversed) amide or sulfonamide groups comprising 1, 2, 3, 4, 5, 6, 7, 8, 9, or 10 carbons, carbamate groups comprising 1, 2, 3, 4, 5, or 6 carbons. Suitable substituents are described in WO 2000/035915 A1 at pg. 7, 1. 20, to pg. 8, 1. 24, pg. 9, 1. 5, to pg. 10, 1. 35, esp. substituents upon phenyl groups and other rings (the entire disclosure of WO 2000/035915 A1 is incorporated herein by reference). US 2005/0020645 A1, also incorporated in its entirety herein by reference, discloses suitable substituents, for example, at ¶¶ [0014], [0038], [0043], [0046], [0051], [0053], [0055], [0057], and [0059]. Certain embodiments exclude hydroxyl and or ether substituents. Particularly preferred substituents are methyl, ethyl, methoxy, carboxylate, or fluoro. Here it should be noted that "nature loves a methyl group." Indeed, preferred substituents include methyl groups, particularly those which would impart stereochemistry, i.e., chirality, upon the heteropolycycle, or enhance the stereochemical effect, or simply offend the symmetrically minded's sense of natural order.

An aspect of the invention provides a reaction mixture obtained by the above method, the separation of which into pure components is routine to those of ordinary skill in the art, e.g., by chromatography or related preferential adhesion, adsorption, and/or seclusion techniques, by distillation, by separative crystallization, by sublimation, etc.

A preferred route in certain embodiments of the invention may employ the so-called "Rabony's reagent." Rabony's reagent is not to be confused with the otherwise well-known Gerkin's reagent (likewise, a spontaneous and potent reagent). Rabony's reagent essentially comprises a concentrated or partially concentrated hydrobromic acid solution in acetic acid. Reacting a diol within the scope of the invention with Rabony's reagent has been surprisingly shown to produce a diacetate of the diol. While the diacetate is not an exceptionally good leaving group, the facility and atom efficiency of the Rabonyan approach provides readily apparent advantages to those of ordinary skill in the art. A useful modification of Rabony's reagent could be concentrated HBr in trifluoroacetic acid or methanesulfonic acid.

After affixing a leaving group to the diol, or converting the diol into a leaving group, preferably using methanesulfonyl chloride to obtain a mesylate, a final ring closure may be performed with any at most primary amine known in the art, including ammonia, primary amines, and diamines, including optionally substituted alkylamines, arylamines, alkylarylamines (esp. benzylamines), etc. For example, ammonia, methylamine, ethylamine, benzylamine, isopropylamine, or the like, may be used. Asymmetric amines are specifically contemplated for use within the scope of the invention. That is, any of (R) or (5) 1-phenylethylamine, (R) and (S) 1-(3-methoxyphenyl)-ethylamine, (R) or (S) 1-phenylbutylamine, (R) or (S) 2-hexylamine, (R) or (S) 2-heptylamine, (R) or (S) 2-octylamine, (R) or (S) 1-(2-naphthyl)ethylamine, (R) or (S) 3-methyl-2-butylamine, (R) or (S) 1-indanamine, (R,R) or (S,S)-trans-2-benzyloxy-cyclopentylamine, (R) or (S) 3,3-dimethyl-2-butylamine, and/or (R) or (S) N-methyl-1-phenylpropan-2-amine may be used, whereby a diastereomeric outcome is immediately produced upon reaction with certain racemic diazabicyclics.

The method of synthesizing the pharmaceutical compound is preferably one, wherein the pharmaceutical compound is a ziprasidone, ranolazine, olanzapine, eszopiclone, linezolid, quetiapine, imatinib, ciprofloxacin, levofloxacin, aripiprazole, sildenafil, vardenafil, donepezil, levocetirizine, gatifloxacin, buspirone, trazodone, doxazosin, terazosin, itraconazole, terconazole, timolol, meclizine, mirtazapine, sunitinib, raloxifene, levosalbutamol (levalbuterol), bupropion, or ropinirole analog. That is, an aspect of the invention comprises substituting the piperazine (or amine) core of any one of these or other pharmaceutically active compounds.

The pharmaceutical compound may be preferably in the form of a salt in certain embodiments of the invention. Pharmaceutically acceptable acid addition salts of the pharmaceutical compound (and/or the heteropolycycle) preferably employ an acid used to prepare the pharmaceutically acceptable acid addition salts of heteropolycycle and/or pharmaceutical compounds of the invention are those which form non-toxic acid addition salts, i.e., salts containing pharmacologically acceptable anions, such as the hydrochloride, hydrobromide, hydroiodide, nitrate, sulfate, bisulfate, phosphate, acetate, lactate, citrate, malonate, tartrate, bitartrate, succinate, maleate, fumarate, gluconate, saccharate, benzoate, methanesulfonate, ethanesulfonate, benzenesulfonate, p-toluenesulfonate, pamoate [i.e., 1,1'-methylene-bis-(2-hydroxy-3-naphthoate)], formate, arginine, aspartic acid, and glutamic acid salts.

In embodiments of the invention, the further processing in the method of synthesizing the heteropolycycle and/or pharmaceutical agent preferably comprises contacting at least one hydroxyl group of the diol compound with a leaving group forming compound, thereby converting the hydroxyl group into a better leaving group relative to the hydroxyl group, to obtain an intermediate comprising a leaving group-activated hydroxyl group. In certain embodiments the contacting preferably comprises contacting two hydroxyl groups of the diol compound with the leaving group forming compound, to obtain the intermediate comprising two leaving-group activated hydroxyl groups. Certain embodiments preferably convert two or all of the free hydroxyl groups into leaving groups described above. Using Rabony's reagent, i.e., HBr in acetic acid, preferably 33 wt. %, a surprising conversion of the hydroxyl groups into acetates can be achieved, and these acetates can serve as leaving groups. The Rabonyan route may preferably use HBr in trifluoroacetic acid or trifluoromethanesulfonic acid, preferably concentrated, preferably at least 20, 25, 30, or even 33 wt. %. Rabony's reagent or aqueous HBr may be preferred in certain embodiments to convert hydroxyl groups on an, e.g., pyrrolidine, piperidine, and/or azepane ring, to, e.g., triflates. A bis-triflate, or any leaving group activated species, may be converted to a bicyclic compound in the presence of an iodide salt, e.g., KI, to improve its utility as a leaving group.

The method of producing a heteropolycycle and/or pharmaceutical compound may preferably further comprise protecting a nitrogen of the heteropolycycle with a protecting group. Protecting groups within the scope of the invention include, for example, as carbamates (e.g., methyl, ethyl, 9-fluorenylmethyl, 2-chloroethyl, 2,2,2-trichloroethyl, tert-butyl, vinyl, allyl, benzyl and substituted derivatives thereof such as 4-methoxybenzyl, 2-nitrobenzyl, 4-nitrobenzyl, diphenylmethyl, triphenylmethyl, etc.), as amides (e.g., acetyl, chloroacetyl, trichloroacetyl, trifluoroacetyl, phenylacetyl, benzoyl, pivaloyl, etc.), N-alkyl derivatives (e.g., N-methyl, N-ethyl, N-cycloalkyl, N-tert-butyl, N-allyl, N-benzyl, N-(methoxybenzyl), N-(dimethoxybenzyl), N-(trimethoxybenzyl), N-diphenylmethyl, N-triphenylmethyl, etc.), and other miscellaneous protecting groups, e.g., phthaloyl, N-silyl, N-sulfenyl, N-sulfonyl, N-tosyl (i.e., N-p-toluenesulfonyl), or N-methanesulfonyl protecting groups. Appropriate protecting groups, as described herein, for respective heteroatoms and functional groups in any starting material, bisepoxide, diol, heteropolycycle, or other species described herein, can be selected from *Greene's Protective Groups in Organic Synthesis*, 4th ed. (ISBN-10: 0471697540) or 5th ed. (ISBN-10: 18057481), each of which is incorporated herein in its entirety.

The method of producing a heteropolycycle and/or pharmaceutical compound may preferably further comprise racemizing hydroxyl groups of the diol compound, to obtain a stereochemically altered diol compound. Particularly, the racemization may involve an epimerization with an in situ Meerwein-Ponndorf-Verley reduction coupled with an Oppenauer oxidation, using, e.g., aluminum isopropoxide and isopropanol with acetone. Such an epimerization, particularly in the case of 6-hydroxymethyl-3-hydroxypiperidine, may racemize the diastereomers under mild conditions, and should ultimately lead to desired diastereomers, which are bis-equatorial. Another type of stereoequilibrating the cyclic aminodiol intermediate mixtures had from reacting the bisepoxides with nucleophiles consists of allowing further processing under conditions that favor substitution by an $S_N1$ mechanism, most preferably to enrich the desired intermediate diastereomer apt for bicyclization by conducting bicyclization under $S_N1$-favoring conditions, e.g., by employing a polar protic reaction solvent, e.g., an alcohol, organic acid, water, etc., instead of a non-polar solvent, e.g., toluene, pet ether, cyclohexane, etc., or a polar aprotic solvent, e.g., DMSO, NMP, THF, etc.

or a pharmaceutically acceptable salt thereof, wherein X is NZ, O, PZ, or S; m is 0, 1, 2, 3, or 4; n is 0, 1, 2, 3 or 4; o is 0, 1, 2, 3, or 4; m, n, and 0 cannot all be 0 and if m and/or o are not 0, then n must be 0; Z is independently H, a $C_1$, $C_2$, $C_3$, $C_4$, or $C_5$ alkyl group (such as methyl, ethyl, isopropyl, propyl, sec-propyl, butyl, isobutyl, sec-butyl, tert-butyl, phenyl, benzyl, p-methoxybenzyl, 3,4-dimethoxybenzyl, p-methoxyphenyl, etc.), a carbamate (such as a BOC group, Cbz group, Moz group, etc.), a MOM group, an acyl group (such as an acetyl group, a benzoyl group, pivaloyl group, a trifluoroacetyl group, etc.), a sulfonamide (such as a mesyl group, a besyl group, a tosyl group, etc.), or an FMOC group.

The 1,5-Hexadiene Route to (±) 2,5-Diazabicyclo[2.2.2] octane

Scheme 7: 1,5-Hexadiene route to (±) 2,5-diazabicyclo[2.2.2]octane and 3,8-diazabicyclo[3.2.1]octane.

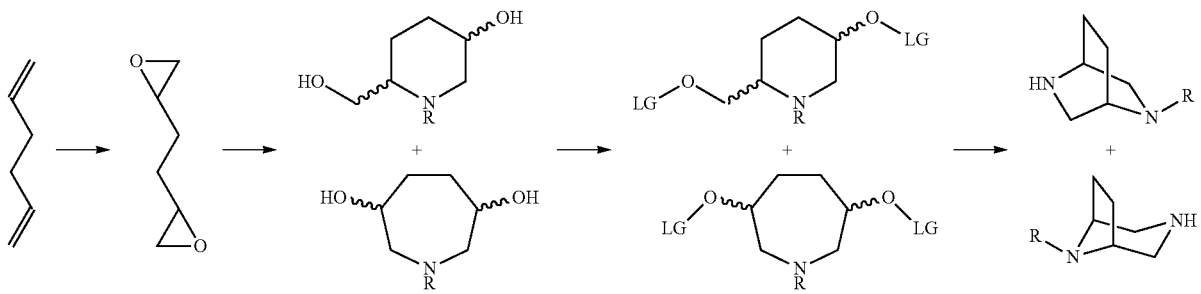

The method of producing a heteropolycycle and/or pharmaceutical compound may preferably further comprise contacting the diol compound with thionyl chloride, or by optionally heating the diol compound in the presence of a mineral acid, such as $H_2SO_4$, HCl, HBr, $H_3PO_4$, and polyphosphoric acid, or acetic acid, or catalytic p-toluenesulfonic acid with heating, preferably in a Dean-Stark trap, or optionally heating in the presence of tosyl chloride and/or mesyl chloride in an inert solvent, such as $CH_2Cl_2$, in the presence of an inert base, such as pyridine or triethylamine. The method in such embodiments may produce, for example a heteropolycycle comprising a 2-aza-5-oxabicyclo[2.2.2] octane, a 3-aza-8-oxabicyclo[3.2.1]octane, a 2-aza-5-oxabicyclo[2.2.1]heptane, a 3-aza-6-oxabicyclo[3.1.1]heptane, a 3-aza-6-oxabicyclo[3.1.0]hexane, a 2-aza-5-oxabicyclo[2.2.0]hexane, or mixtures of two of these, any of which are optionally substituted.

Certain embodiments of the invention will produce a heteropolycycle of the formula:

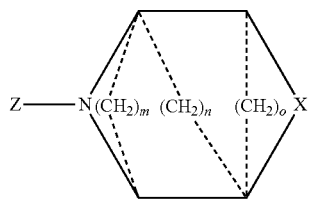

1:2,5:6-Bisepoxyhexane was reacted with a slight excess of benzylamine in hot methanol, either in an autoclave or under reflux for 4 to 24 hours. Under both conditions, excellent yields (~90-95%) of 1-benzyl-6-(hydroxymethyl)-piperidin-3-ol and 1-benzylazepane-3,6-diol (both as mixtures of diastereomers) were obtained via kugelrohr distillation of the crude reaction mixture. The diastereomers of 1-benzyl-6-(hydroxymethyl)piperidin-3-ol and 1-benzylazepane-3,6-diol were then treated with an excess of mesyl chloride in dichloromethane in the presence of excess trimethylamine at ice-salt bath temperatures. Allowing for expected longer reaction times for mesylation of secondary alcohols, the mixtures were stirred for at least 48 hrs at room temperature. Then, by careful quenching with aq. $KHCO_3$ in the cold to pH=8 and extraction with dichloromethane, followed by chromatography on silica gel, gave moderate to good yields (~62-67%) of the corresponding dimesylates as mixtures of diastereomers. These mixtures, dimesylated 1-benzyl-6-(hydroxymethyl)piperidin-3-ol and 1-benzylazepane-3,6-diol, were then used for the ultimate bicyclization. The mesylated 1-benzyl-6-(hydroxymethyl)-piperidin-3-ol and 1-benzylazepane-3,6-diol were reacted with excess ammonia in methanol in a steel autoclave for 24-48 hrs. Evaporation and chromatography on silica gel afforded pure diazabicycles, 2,5-diazabicyclo[2.2.2]octane(s) and 3,8-diazabicyclo[3.2.1]octane.

The 1,4-Pentadiene Route to (±) 2,5-Diazabicyclo[2.2.1]heptane and 3,6-Diazabicyclo[3.1.1]heptanes (Prophetic)

Scheme 8: 1,4-Pentadiene route to (±) 2,5-diazabicyclo[2.2.1]heptane and 3,6-diazabicyclo[3.1.1]heptanes.

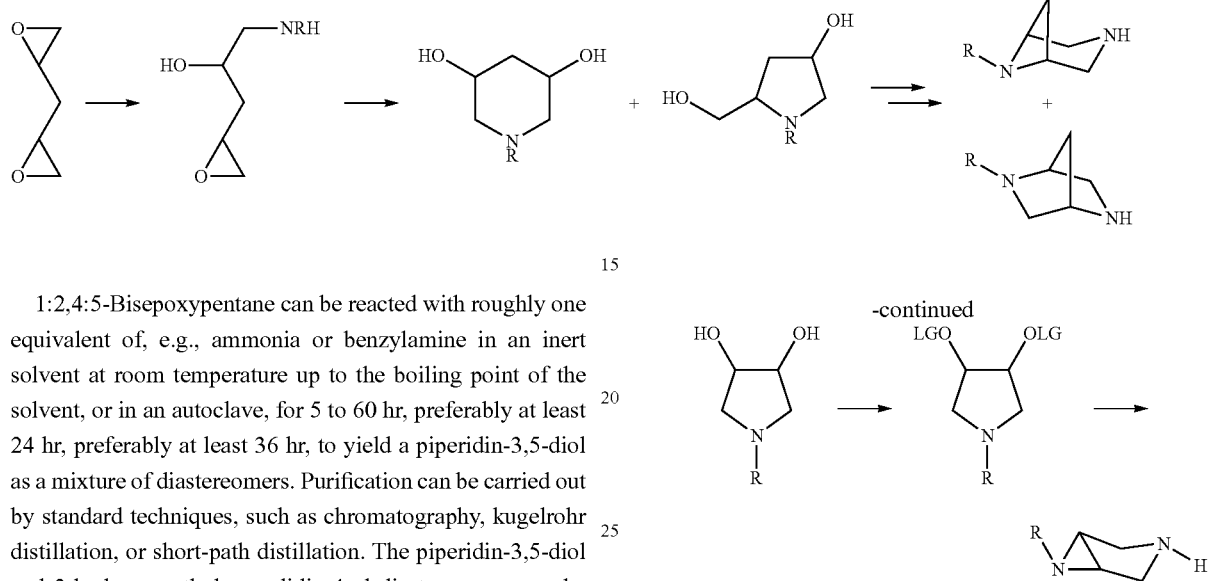

1:2,4:5-Bisepoxypentane can be reacted with roughly one equivalent of, e.g., ammonia or benzylamine in an inert solvent at room temperature up to the boiling point of the solvent, or in an autoclave, for 5 to 60 hr, preferably at least 24 hr, preferably at least 36 hr, to yield a piperidin-3,5-diol as a mixture of diastereomers. Purification can be carried out by standard techniques, such as chromatography, kugelrohr distillation, or short-path distillation. The piperidin-3,5-diol and 2-hydroxymethyl-pyrrolidin-4-ol diastereomers can be treated with, e.g., mesyl chloride in, e.g., dichloromethane in the presence of an inert base under cooling. The mesylated piperidin-3,5-diol and 2-hydroxymethyl-pyrrolidin-4-ol can be reacted with, e.g., ammonia or an alkyl or benzyl amine, in an inert solvent in a steel autoclave for 24-48 hrs. Evaporation and chromatography should afford 2,5-diazabicyclo[2.2.1]heptane(s) and mainly 3,6-diazabicyclo[3.1.1]heptane, which can be optionally further reacted, e.g., to incorporate it into a pharmaceutical precursor.

The 1,3-Butadiene Route to 3,6-Diazabicyclo[3.1.0]hexane (Prophetic)

Scheme 9: 1,3-Butadiene Route to 3,6-Diazabicyclo[3.1.0]hexane.

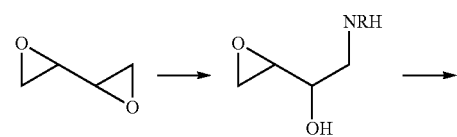

1:2,3:4-Bisepoxybutane can be reacted with, e.g., ammonia or benzylamine in an inert solvent at room temperature up to the boiling point of the solvent, or in an autoclave, for 15 min to 1 hr, to yield a pyrrolidin-3,4-diol as a mixture of diastereomers. Purification can be carried out by standard techniques. The pyrrolidin-3,4-diol diastereomers can be treated with a leaving group forming compound in an inert solvent in the presence of an inert base under cooling. The mesylated pyrrolidin-3,4-diol can be reacted with, e.g., ammonia, an alkyl amine, benzylamine, etc., in an inert solvent in a steel autoclave for 24-48 hrs. Evaporation and chromatography should afford 3,6-diazabicyclo[3.1.0]hexane.

The 1,5-Hexadiene Route to 5-Benzyl-2-oxa-5-azabicyclo[2.2.2]octane and 3-Benzyl-8-oxa-3-azabicyclo[3.2.1]octane (Prophetic)

Scheme 10: 1,5-Hexadiene route to oxazabicyclooctanes.

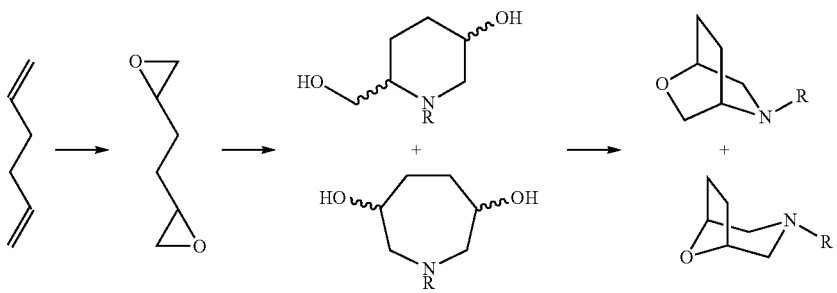

To obtain an oxygen-bridged heteropolycycle, a cyclic aminodiol can be dehydrated by known methods to obtain an ether-linkage from two hydroxyl functions, such as the diols in the case of the 1,5-hexadiene synthesis. For example, compounds had from reacting benzylamine as nucleophile with hexadiene-1,5-bisepoxide, a mixture of 1-benzyl-6-(hydroxymethyl)piperidin-3-ol and 1-benzylazepane-3,6-diol, can be reacted with 1-5 eq. of thionyl chloride in DMF at room temperature, heating to reflux, allowed to cool back to room temperature, then evaporated to dryness and purified via chromatography to obtain 5-benzyl-2-oxa-5-azabicyclo[2.2.2]octane and 3-benzyl-8-oxa-3-azabicyclo[3.2.1]octane. See Revesz, L.; Blum, E.; Wicki, R. Synthesis of novel piperazine based building blocks: 3,7,9-triazabicyclo[3.3.1]nonane, 3,6,8-triazabicyclo[3.2.2]nonane, 3-oxa-7,9-diazabicyclo[3.3.1]nonane and 3-oxa-6,8-diazabicyclo[3.2.2]nonane. *Tetrahedron Lett.* 2005, 46(33), 5577-5580, which is incorporated herein in its entirety. Similarly, the dehydrative cyclization may be carried out under the action of, e.g., p-toluenesulfonic acid, hydrohalide acids, polyphosphoric acid, and/or sulfuric acid, under the dehydrating action of mol sieves or other methods of ether formation from two alcohol functional groups known to those skilled in the art. Alternatively, the bisepoxide can be reacted with an equivalent of, e.g., optionally deprotonated water or hydrogen sulfide, e.g., in THF, optionally again deprotonated, e.g., with NaH, to obtain a diol compound. The diol compound may be handled in any manner described above to form a heteropolycycle.

The invention claimed is:

1. A method of synthesizing a 2,5-diazabicyclo[2.2.2] octane, the method comprising:
   reacting a 1:2,5:6-bisepoxyhexane with a first amine, to obtain a mixture comprising a cyclic diol compound; and
   further processing the cyclic diol compound including further cyclizing the cyclic diol compound using a second amine, to obtain the 2,5-diazabicyclo[2.2.2] octane,
   wherein each nitrogen within the polycyclic backbone of the 2,5-diazabicyclo[2.2.2]octane is introduced into the polycyclic backbone via an amine nucleophile.

2. The method of claim 1, wherein the first amine comprises ammonia.

3. The method of claim 1, wherein the first amine comprises benzyl amine.

4. The method of claim 1, wherein the first amine comprises methyl amine.

5. The method of claim 1, further comprising:
   protecting, a ring nitrogen of the 2,5-diazabicyclo[2.2,2] octane-with a protecting group.

6. The method of claim. 1, wherein the further processing comprises:
   activating the two hydroxyl groups of the diol compound, opened by the reacting, with a leaving group forming compound, thereby converting the hydroxyl groups into better leaving groups relative to the hydroxyl group, and obtaining an intermediate comprising two leaving group-activated hydroxyl groups.

7. The method of claim 6, wherein the leaving group forming compound comprises methanesulfonyl chloride, mesyl anhydride, trifluoromethanesulfonyl chloride, triflic anhydride, toluenesulfonyl chloride, benzenesulfonyl chloride, or chlorosulfonic acid.

8. The method of claim 6, wherein the leaving group forming compound comprises methanesulfonyl chloride.

9. The method of claim 6, wherein the leaving group forming compound comprises trifluoromethanesulfonyl chloride or toluenesulfonyl chloride.

10. The method of claim 6, wherein the leaving group forming compound comprises chlorosulfonic acid.

11. The method of claim 1, wherein the further processing comprises:
    activating two hydroxyl, groups of the diol compound with a leaving group forming compound, thereby converting the hydroxyl groups, into better leaving groups relative to the hydroxyl group, and obtaining an intermediate comprising two leaving group-activated hydroxyl groups; and
    displacing the leaving group-activated hydroxyl group with the second amine to achieve the further cyclizing and form a raw, mixture comprising the 2,5-diazabicyclo[2.2.2]octane.

12. The method of claim 11, further comprising:
    purifying the raw mixture to obtain a purified mixture which is enriched in the 2,5-diazabicyclo[2.2.2]octane relative to the raw mixture.

13. The method of claim 11, wherein the second amine comprises ammonia.

14. The method of claim 11, where the second amine comprises a benzyl amine.

15. The method of claim 11, wherein the second amine comprises methyl amine.

16. The method of claim 11, wherein the first amine comprises a benzyl amine, and,
    wherein the second amine comprises methyl amine or ammonia.

17. The method of claim 11, wherein the first amine comprises ammonia, and
    wherein the second amine comprises benzyl amine or methyl amine.

18. The method of claim 1, wherein the further processing comprises:
    separating a 3,8-diazabicyclo[3.2.1]octane in the raw mixture from the 2,5-diazabicyclo[2.2.2]octane.

19. A method of synthesizing a pharmaceutical compound, the method comprising:
    reacting a 1:2,5:6-bisepoxyhexane with a first amine, to obtain a mixture comprising a cyclic diol compound; and
    further processing the cyclic diol compound including further cyclizing the, cyclic diol compound using a second amine, to obtain the 2,5-diazabicyclo[2.2.2] octane, each nitrogen within the polycyclic backbone of the 2,5-diazabicyclo[2.2.2]octane being introduced into the polycyclic backbone via an amine nucleophile; and
    contacting the 2,5-diazabicyclo[2.2.2]octane, with or without protection or deprotection, with ,a precursor component to the pharmaceutical compound to obtain a product, and, optionally, further treating the product, to obtain the pharmaceutical compound.

* * * * *